US00PP31053P3

(12) United States Plant Patent
Klemm et al.

(10) Patent No.: US PP31,053 P3
(45) Date of Patent: Nov. 12, 2019

(54) ***DAHLIA* PLANT NAMED 'KLEDH17008'**

(50) Latin Name: ***Dahlia* sp.**
Varietal Denomination: KLEDH17008

(71) Applicant: Klemm+Sohn GmbH & Co. KG, Stuttgart (DE)

(72) Inventors: Nils Klemm, Stuttgart (DE); Maike Boxriker, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/998,601

(22) Filed: Aug. 16, 2018

(65) Prior Publication Data

US 2019/0289761 P1 Sep. 19, 2019

(30) Foreign Application Priority Data

Mar. 13, 2018 (QZ) ..... PBR 2018/0756

(51) Int. Cl.
*A01H 5/02* (2018.01)
*A01H 6/14* (2018.01)

(52) U.S. Cl.
USPC ..... Plt./321
CPC ..... *A01H 6/144* (2018.05)

(58) Field of Classification Search
USPC ..... Plt./321
See application file for complete search history.

(56) References Cited

PUBLICATIONS

UPOV hit on *Dahlia* plant named, 'KLEDH17008', QZ PBR 20180756, filed Mar. 14, 2018.*

* cited by examiner

*Primary Examiner* — Anne Marie Grunberg
(74) *Attorney, Agent, or Firm* — Barbara Campbell; Cochran Freund & Young LLC

(57) ABSTRACT

A new *Dahlia* plant particularly distinguished by yellow flowers and an upright habit, is disclosed.

1 Drawing Sheet

Genus and species: *Dahlia* sp.
Variety denomination: 'KLEDH17008'.

CROSS-REFERENCE TO RELATED APPLICATIONS

This application claims priority to and the benefit of European Community Plant Variety Rights application filed on Mar. 13, 2018, File No. 2018/0756, the entire contents of which are incorporated herein by reference for all purposes.

'KLEDH17008' has not been made publicly available for more than one year prior to the effective filing date of the present application.

BACKGROUND OF THE NEW PLANT

The present invention comprises a new and distinct variety of *Dahlia*, botanically known as *Dahlia* sp., and hereinafter referred to by the variety name 'KLEDH17008'. 'KLEDH17008' originated from a cross-pollination conducted between September to November 2013 in Stuttgart, Germany between the proprietary female *Dahlia* variety 'KLEDH13033' (U.S. Plant Pat. No. 26,741) and the commercial male *Dahlia* variety 'Dahlette Surprise Louise' (patent status unknown).

The seeds from the cross-pollination were sown and plants were grown in a greenhouse for evaluation, where an individual plant designated 'KLEDH17008' was selected from the group in May 2014 of plants in Stuttgart, Germany. In February 2015, 'KLEDH17008' was first vegetatively propagated by terminal cuttings. 'KLEDH17008' was found to reproduce true to type in successive generations of asexual propagation via terminal cuttings.

SUMMARY

The following are the most outstanding and distinguishing characteristics of this new variety when grown under normal horticultural practices in Stuttgart, Germany.

1. Yellow flowers; and
2. An upright plant habit.

DESCRIPTION OF THE PHOTOGRAPH

The following detailed descriptions set forth the distinctive characteristics of 'KLEDH17008'. The data which define these characteristics were collected from asexual reproductions carried out in Stuttgart, Germany. The photo is of a 13-week-old plant grown indoors in Stuttgart, Germany under greenhouse conditions in April 2014. Color references are to The R.H.S. Colour Chart of The Royal Horticultural Society of London (R.H.S.), $5^{th}$ edition (2007).

DESCRIPTION OF THE NEW VARIETY

The following detailed descriptions set forth the distinctive characteristics of 'KLEDH17008'. The data which define these characteristics were collected from asexual reproductions carried out in Stuttgart, Germany in May 2018. Data was collected on plants potted in week 11 and grown in a controlled greenhouse environment approximating those generally used in commercial production, pinched once, with a growth regulator, and under natural light. Color references are to The R.H.S. Colour Chart of The Royal Horticultural Society of London (R.H.S.), 5th edition (2007).

Classification:

*Family*.—Asteraceae.

*Botanical*.—*Dahlia* sp.

*Common*.—*Dahlia*.

*Designation*.—'KLEDH17008'.

Parentage:

*Female parent*.—The proprietary female *Dahlia* variety 'KLEDH13033' (U.S. Plant Pat. No. 26,741).

*Male parent*.—The commercial male *Dahlia* variety 'Dahlette Surprise Louise' (patent status unknown).

Plant:

*Plant and growth habit*.—Upright, free basal branching, and inflorescences held above the foliar plane.

*Height*.—40.0 cm.

*Diameter*.—30.0 cm.

*Propagation*.—Terminal cuttings.

*Time to produce a rooted young plant*.—3 weeks.

*Root description*.—Light tan in color (RHS 155C) and fine.

*Rooting habit*.—Freely branching and moderately dense.

Lateral branches:

*Length*.—22.0 cm.

*Diameter*.—0.3 cm.

*Internode length*.—7.0 cm.

*Aspect*.—Outwardly spreading.

*Strength*.—Strong.

*Texture*.—Smooth.

*Color*.—RHS 144A.

Foliage/leaves:

*Arrangement*.—Leaves are opposite, pinnately compound.

*Length*.—11.0 cm.

*Width*.—4.5 cm.

*Shape*.—Oval.

*Apex*.—Acute.

*Base*.—Acute.

*Margin*.—Moderately serrate.

*Immature leaf color*.—Upper surface: RHS 146A. Lower surface: RHS 144B.

*Mature leaf color*.—Upper surface: RHS 146B. Lower surface: RHS 144B.

*Texture* (*both upper and lower surfaces*).—Smooth.

*Venation pattern*.—Pinnate.

*Venation color* (*both surfaces*).—RHS 145A.

*Petioles*.—Length: 2.5 cm. Diameter: 0.3 cm. Texture (both upper and lower surfaces): Smooth. Color: Upper surface: RHS 144C. Lower surface: RHS 145B.

Buds:

*Height*.—1.4 cm.

*Diameter*.—1.0 cm.

*Shape*.—Oblate.

*Color*.—RHS 150A.

Inflorescence:

*Appearance and arrangement*.—Flower head is semi-upright, held above the foliar plane.

*Fragrance*.—Present.

*Time to flower*.—In the winter, about 3 months after planting; in the summer, about 2 months after planting.

*Post-production longevity*.—Plants flower continuously from spring through autumn.

*Inflorescence diameter*.—6.5 cm.

*Inflorescence depth*.—3.0 cm.

*Disc diameter*.—1.0 cm.

*Receptacle height*.—About 1.0 cm.

*Receptacle diameter*.—4.0 cm.

*Receptacle color*.—RHS 145A.

Ray florets:

*Quantity per inflorescence*.—About 50.

*Length*.—2.5 cm.

*Width*.—1.5 cm.

*Shape*.—Elliptic.

*Apex*.—Obtuse.

*Base*.—Moderately involute, rounded.

*Margin*.—Entire.

*Aspect*.—Semi-upright.

*Texture* (*both upper and lower surfaces*).—Smooth.

*Color, immature*.—Upper surface: RHS 2B. Lower surface: RHS 1B.

*Color, mature*.—Upper surface: RHS 2B. Lower surface: RHS 1B.

Disc florets:

*Quantity per inflorescence*.—About 30.

*Length*.—About 1.5 cm.

*Diameter*.—0.2 cm.

*Shape*.—Elliptic.

*Texture* (*both the upper and lower surfaces*).—Smooth.

*Color, immature* (*both upper and lower surfaces*).—RHS 1D.

*Color, mature* (*both upper and lower surfaces*).—RHS 3B.

Phyllaries:

*Quantity per inflorescence*.—8.

*Length*.—2.0 cm.

*Width*.—0.6 cm.

*Shape*.—Elliptic.

*Apex*.—Acute.

*Base*.—Acute.

*Margin*.—Entire.

*Texture* (*both upper and lower surfaces*).—Smooth.

*Color*.—Upper surface: RHS 150A. Lower surface: RHS 150B.

Peduncles:

*Length, terminal peduncle*.—22.0 cm.

*Length, axillary peduncle*.—9.0 cm.

*Diameter*.—0.3 cm.

*Aspect*.—Semi-upright.

*Strength*.—Strong.

*Texture*.—Smooth.

*Color*.—RHS 145A.

Reproductive organs:

*Androecium*.—Present on disc florets only. Quantity per floret: 4. Filament length: 0.4 cm. Filament color: RHS 1D. Anther shape: Long lanceolate. Anther length: 0.5 cm. Anther color: RHS 14B. Pollen amount: Abundant. Pollen color: RHS 23A.

*Gynoecium*.—Quantity per floret: 1. Pistil length: 1.0 cm. Style length: 0.5 cm. Style color: RHS 5A. Stigma shape: Lanceolate pinnate. Stigma color: RHS 14A. Ovary color: RHS 8D.

Fruit and seed set: No fruit and seed set observed.

Disease and pest/insect resistance: No disease and pest/insect resistance observed.

COMPARISON WITH PARENTAL LINES AND KNOWN VARIETIES

'KLEDH17008' is a distinct variety of *Dahlia* and is distinguished from its parents as described in Table 1.

TABLE 1

Comparison with Parental Lines

| Characteristic | 'KLEDH17008' | Female Parent 'KLEDH13033' | Male Parent 'Dahlette Surprise Louise' |
|---|---|---|---|
| Ray floret color | Yellow | Yellow with red eyes | Purple with white eyes |

'KLEDH17008' is a distinct variety of *Dahlia* and is most similar to the commercial *Dahlia* varieties 'KLEDH13033' (U.S. Plant Pat. No. 26,741), 'Dalina' (unpatented) and 'La Bella' (unpatented). Differences between the varieties are described in Table 2 and Table 3.

TABLE 2

Comparison with Similar Variety

| Characteristic | 'KLEDH17008' | 'KLEDH13033' |
|---|---|---|
| Ray floret color | Yellow | Yellow with red-eyes |

TABLE 3

Comparison with Similar Varieties

| Characteristic | 'KLEDH17008' | 'Dalina' | 'La Bella' |
|---|---|---|---|
| Leaf Size | Larger than 'Dalina' and 'La Bella' | Smaller than 'KLEDH17008' | Smaller than 'KLEDH17008' |

We claim:

1. A new and distinct variety of *Dahlia* plant designated 'KLEDH17008' as illustrated and described herein.

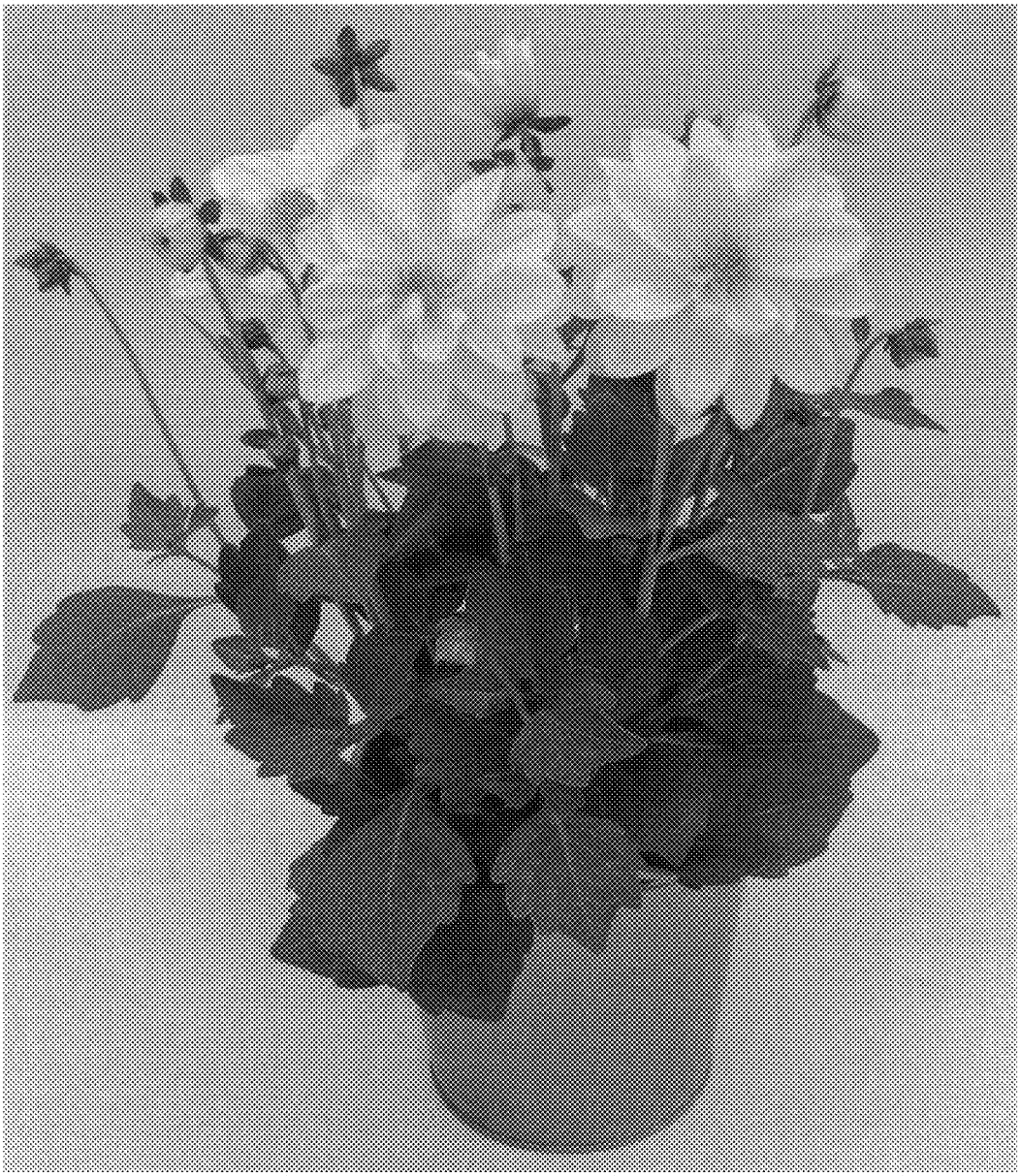

* * * * *